United States Patent [19]

Bosserelle

[11] Patent Number: 4,740,432
[45] Date of Patent: Apr. 26, 1988

[54] VEGETABLE ORIGIN FATTY SUBSTANCE COMPOSITION AND COSMETIC COMPOSITIONS CONTAINING THE SAME

[76] Inventor: Micheline Bosserelle, 29, Rue Pierre Nicole, F-75005 Paris, France

[21] Appl. No.: 885,182

[22] Filed: Jul. 14, 1986

[30] Foreign Application Priority Data

Jul. 17, 1985 [FR] France ................. 85 10976

[51] Int. Cl.$^4$ .................. A61K 7/06; A61K 7/42; A61K 7/44
[52] U.S. Cl. ...................... 424/59; 424/60; 424/70; 514/167; 514/458; 514/474; 514/725; 514/783; 514/801; 514/847; 514/938; 514/969
[58] Field of Search .............. 424/70, 59; 514/969

[56] References Cited

FOREIGN PATENT DOCUMENTS 2232323 1/1973 Fed. Rep. of Germany ........ 424/70
2250866 4/1973 Fed. Rep. of Germany ........ 424/70

OTHER PUBLICATIONS

Wood et al., United States Dispensatory, 1926, 21st edition, pp. 12–51.
Steinmetz, Codex Vegetabilis, 1957, p. 278.
Ellingwood, Materia Medica and Therapeutics, 1907, 6th edition, pp. 673 and 674.
Pharmaceutical Formulas, 1946, vol. II, pp. 241–248 & 250 to 253.

*Primary Examiner*—Dale R. Ore
*Attorney, Agent, or Firm*—Fleit, Jacobson, Cohn & Price

[57] ABSTRACT

Vegetable fatty substance composition for use in cosmetics containing: fatty acid triglycerides 85–94%, fatty acid esters containing 40 carbon atoms 7–14%, vitamins 0.01–1.0%, antioxidant 0.5–1.5% if required.

This composition is prepared by malaxing in the heated state, at a temperature not exceeding 50° C., fatty acid triglycerides to which the fatty acid ester is added and after mixing well, the vitamins, and if required, the antioxidant, are added.

The fatty substance composition advantageously replaces the animal origin fatty substances in cosmetic compositions.

12 Claims, No Drawings

VEGETABLE ORIGIN FATTY SUBSTANCE COMPOSITION AND COSMETIC COMPOSITIONS CONTAINING THE SAME

The invention relates to a vegetable origin fatty substance composition intended for use in cosmetic compositions.

It is known that cosmetic compositions, and more particularly cosmetic compositions for the treatment of skin and hair, contain fatty components. Various fatty substances of animal origin have been used in cosmetic compositions, especially mink, marmot and green turtle oils.

However, these fatty substances of animal origin have various disadvantages.

They are often contaminated with blood and other impurities and quickly become rancid. Besides, compared with constituents which have a good compatibility with the epidermis, these animal origin fatty substances also contain constituents, especially short-chain fatty acids, which irritate the skin.

Finally, the production of these animal origin fatty substances requires the killing of a large number of animals, which is likely to disturb the ecological balance.

Consequently, there is a need for replacing the animal origin fatty substances intended for use in cosmetic compositions by vegetable origin fatty substances.

The Applicant has discovered that a vegetable origin fatty substance composition, hereinafter called CHELONINE is suitable for advantageously replacing the animal origin fatty substances, and more particularly, green turtle oil, in cosmetic uses.

In comparison with animal oils, and more particularly in comparison with green turtle oil, chelonine has the advantage of a better compatibility with the epidermis, because of the absence of fatty acids containing 12 carbon atoms or less than 12 carbon atoms, and because of the presence of at least one fatty acid ester containing 40 carbon atoms. Additionally, the presence of this $C_{40}$ ester ensures a greater stability thereof against oxidation, and consequently, an improved storage. Chelonine consists of 85 to 94%, and preferably from 88 to 92%, of triglycerides of fatty acids, from 7 to 14%, and preferably from 8.5 to 11.5%, and more preferably 10% of fatty acid ester containing 40 carbon atoms, from 0.01 to 1%, and preferably from 0.1 to 0.5%, of vitamins, and if required, from 0.5 to 1.5% of an antioxidant. The average fatty acid composition of the triglycerides, expressed as % by weight, is as follows:
myristic acid: 0.35-0.7%, and preferably 0.45-0.6%
palmitic acid: 68-76%, and preferably 70-74%
stearic acid: 4-7.5%, and preferably 5.5-6.7%
linoleic acid: 8-10.5%, and preferably 8.5-9.5%
linolenic acid: 0.5-2%, and preferably 0.6-1.6%
oleic acid: 8-14%, and preferably 10.3-12.3%.

In the fatty acid triglycerides, the proportion of unsaturated fatty acids relative to the total fatty acids is 15 to 25%, and preferably, from 18.5 to 20.5%.

The fatty acid ester containing 40 carbon atoms advantageously consists of a fatty acid chosen from the group consisting of the following acids:
icosanedioic acid, icosanoic acid or arachidic acid, containing 20 carbon atoms,
docosanoic or behenic acid
cis-13-docosenoic or erucic acid
trans-13-docosenoic acid or isoerucic acid
13-docosynoic acid or behenolic acid containing 22 carbon atoms.

When the fatty acid forming the $C_{40}$ ester contains 20 carbon atoms, the alcohol will be chosen from alcohols which also contain 20 carbon atoms:
1-icosanol or arachidyl alcohol
2-icosanol
9-octadecan-1-ol or elaidyl alcohol.

When the fatty acid of the $C_{40}$ ester contains 22 carbon atoms, the alcohols will advantageously be chosen from the following alcohols containing 18 carbon atoms:
octadecan-1-ol or stearyl alcohol
cis-9-octadecan-1-ol or oleyl alcohol
trans-9-octadecan-1-ol or elaidyl alcohol.

A fatty acid ester consisting of an acid containing 22 carbon atoms and an alcohol containing 18 carbon atoms is preferred.

Chelonine advantageously contains from 0.01 to 1.0%, and preferably from 0.1 to 0.5%, of vitamins chosen from the group consisting of vitamins A, E, F, H, D. It also advantageously contains an antioxidant in a quantity of between 0.5 and 1.5% of the total weight of the composition.

Chelonine keeps well, has a good compatibility with the epidermis, it is slightly astringent and consequently does not dilate the skin and imparts to the latter a soft and pleasant touch.

An advantageous composition of chelonine, expressed in % by weight, is as follows:
fatty acid triglycerides: 89%
fatty acid ester containing 40 carbon atoms: 10%
vitamins: 0.1 to 0.5%
antioxidant: 0.5 to 1.5%
total: 100%

Fatty acid composition of the triglycerides:
myristic acid: 0.5%
palmitic acid: 71.9%
stearic acid: 6.1%
linoleic acid: 9.0%
linolenic acid: 1.1%
oleic acid: 11.35%
total: 100%

Chelonine may advantageously be prepared in a reactor equipped for stirring and with heating and cooling means.

The triglycerides are mixed in the heated state between 35° and 50° C., without exceeding this latter temperature, under a stream of nitrogen, with stirring. After melting the triglycerides, the $C_{40}$ fatty acid ester is added at a temperature of between 45° and 50° C. The malaxing is continued, allowing the mixture to cool to approximately 20° C. at the same time. The vitamins and the antioxidant are added at this temperature and the stirring is continued at ambient temperature for 24 hours. The stability is checked by determining the percentage of peroxide.

Chelonine is advantageously used in various cosmetics for the treatment and care of hair and skin, especially in shampoos, after-shampoo compositions, face, hand and body milks and creams, sunscreen creams, anti-wrinkle creams and similar compositions.

Chelonine is used in cosmetic compositions in a proportion of 0.05 to 30%, and preferably from 0.1 to 15% by weight relative to the total weight of the composition.

The use of chelonine is illustrated by the non-limiting examples which follow, in which the percentages are expressed by weight.

EXAMPLE 1

A shampoo which has the following composition is prepared:
sorbitan monolaurate, polyoxyethylenated with 20 moles of ethylene oxide, manufactured under the name "TWEEN 20" by ATLAS: 10%
sorbitan monooleate, polyoxyethylenated with 20 moles of ethylene oxide, manufactured under the name "TWEEN 80" by ATLAS: 5%
polyoxyethylenated fatty acid esters manufactured under the name "ALATONE 289" by ATLAS: 10%
chelonine: 0.1%
aqueous solution of alkyl dimethyl hydroxyethyl ammonium chloride: 5%
1-alkyl ($C_{12}$) amido-3-dimethyl ammonio-propane-3-carboxymethylbetaine: 30%
water: 37.6%
liquid extract of aloe leaf: 2%
preservative: 0.2%
perfume: 0.1%
total: 100%

EXAMPLE 2

A body milk which has the following composition and which is in the form of an oil-in-water emulsion is prepared:
(A) self-emulsifying glycerol monostearate, manufactured under the name "ARLACEL 165" by ATLAS: 8%
chelonine: 1%
mixture of saturated $C_8$–$C_{10}$ fatty acid triglycerides originating from coconut oil, sold under the name "MIGLIOL 812" by DYNA-FRANCE: 5%
perhydrosqualene: 7%
sesame oil: 2%
(B) glycerine: 5%
water: 69.7%
vegetable extracts: 2%
preservatives: 0.15%
perfumes: 0.15%

EXAMPLE 3

The sunscreen cream which has the following composition and which is in the form of a water-in-oil emulsion:
(A) Vaseline with emulsifying lanolin alcohols: 45%
2-hydroxy-4-methoxybenzophenol, manufactured under the name "EUSOLEX 4360" by MERCK: 3%
4-tert-butyl-4'-methoxydibenzoylmethane, manufactured und the name "PARSOL 1789" by GIVAUDAN: 1%
chelonine: 5%
butyl hydroxytoluene-ascorbin palmitate-citric acid, manufactured under the name "OXYNEX 2004" by MERCK: 0.04%
(B) liquid sorbitol F: 3%
water: 42.93%
preservative, sufficient quantity:
perfume, sufficient quantity:
total: 100%

EXAMPLE 4

An anti-wrinkle cream which has the following composition and which is in the form of an oil-in-water emulsion:
(A) mixture of $C_8$–$C_{10}$ saturated fatty acid triglycerides originating from the fractionation of coconut oil, solid under the name "MIGLIOL 812" by DYNA-FRANCE: 6%
4-tert-butyl-4'-methoxydibenzoylmethane sold under the name "PARSOL 1789" by GIVAUDAN: 2%
chelonine: 14%
perhydrosqualene: 3.98%
sesame oil: 2%
self-emulsifying glycerol monostearate, manufactured under the name "ARLACEL 165" by ATLAS: 8%
sorbitan monostearate, polyethoxylated with 20 moles of ethylene oxide, manufactured under the name "TWEEN 60" by ATLAS: 2%
cetyl alcohol: 2%
(B) water: 49.97%
moisturising complex (NMF): 3%
sodium hyaluronate: 0.2%
skin cell extracts: 1%
liver cell extracts: 1%
liquid extract of aloe leaves: 2%
collagen: 3%
preservative in sufficient quantity:
perfumes in sufficient quantity:
total: 100%

I claim:
1. Fatty substance composition comprising in % by weight of the total composition:
fatty acid triglycerides: 85 to 94%
at least one fatty acid ester containing 40 carbon atoms: 7 to 14%
vitamins: 0.01 to 1.0%
antioxidant: 0.5 to 1.5%
the average fatty acid composition of the triglycerides, expressed in % by weight, being as follows:
myristic acid: 0.35–0.7%
palmitic acid: 68–76%
stearic acid: 4–7.5%
linoleic acid: 8–10.5%
linolenic acid: 0.5–2%
oleic acid 8–14%
the fatty acid esters being selected from the the group comprising:
(i) fatty acid esters derived from a fatty acid selected from the group consisting of icosanedioic acid, icosanoic acid and arachidic acid, and a fatty alcohol selected from the group consisting of 1-icosanol, 2-icosanol and 9-octadecan-1-ol, and
(ii) fatty acid esters derived from a fatty acid selected from the group consisting of docosanoic acid, cis-13-docosenoic acid, trans 13-docosenoic acid, and 13 docosynoic acid and a fatty alcohol selected from the group consisting of octadecan-1-ol, cis-9-octadecan-1-ol and trans-9-octadecan-1-ol.

2. Composition according to claim 1, comprising in % by weight of the total weight of the composition:
fatty acid triglycerides: 88–92%
at least one fatty acid ester containing 40 carbon atoms: 8.5–11.5%
vitamins: 0.1–0.5%
antioxidant: 0.5–1.5%.

3. Composition according to claim 1, characterized in that the content of fatty acid esters containing 40 carbon atoms is of 8.5 to 11.5% by weight of the total weight of the composition.

4. Composition according to claim 1, characterized in that the content of fatty acid esters containing 40 carbon atoms is of 10% of the total weight of the composition.

5. Composition according to claim 1, characterized in that the average fatty acid composition of the triglycerides, expressed in % by weight, is as follows
myristic acid: 0.45–0.6%
palmitic acid: 70–74%
stearic acid: 5.5.–6.7%
linoleic acid: 8.5–9.5%
linolenic acid: 0.6–1.6%
oleic acid: 10.3–12.3%.

6. Composition according to claim 1, characterized in that the average fatty acid composition of the triglycerides, expressed in % by weight, is as follows:
myristic acid: 0.55%
palmitic acid: 71.9%
stearic acid: 6.1%
linoleic acid 9%
linolenic acid: 1.1%
oleic acid: 11.35%.

7. Composition according to claim 1 also containing vitamins chosen from the group consisting of vitamins A, E, F, H and D.

8. Composition according to claim 1, wherein in the fatty acid triglycerides, the proportion of unsaturated fatty acids relative to the total fatty acids is of 15 to 25%.

9. Composition according to claim 8, characterized in that in the fatty acid triglycerides, the proportion of unsaturated fatty acids relative to the total fatty acids is of 18.5 to 20.5%.

10. Cosmetic composition for the care of skin intended for use in face, hand and body milks and creams, sunscreen creams, and anti-wrinkle creams comprising a vegetable origin fatty substance composition comprising in % by weight of the total composition:
fatty acid triglycerides: 85 to 94%
fatty acid ester containing 40 carbon atoms: 7 to 14%
vitamins: 0.01 to 1.0%
antioxidant: 0.5 to 1.5%
    the average fatty acid composition of the triglycerides, expressed in % by weight, being as follows:
myristic acid: 0.35–0.7%
palmitic acid: 68–76%
stearic acid: 4–7.5%
linoleic acid: 8–10.5%
linolenic acid: 0.5–2%
oleic acid: 8–14%.

11. Cosmetic composition for the care of hair intended for use in shampoos and after-shampoo rinses, comprising a vegetable origin fatty substance composition comprising in % by weight of the total composition:
fatty acid triglycerides: 85 to 94%
fatty acid ester containing 40 carbon atoms: 7 to 14%
vitamins: 0.01 to 1.0%
antioxidant: 0.5 to 1.5%
    the average fatty acid composition of the triglycerides, expressed in % by weight, being as follows:
myristic acid 0.35–0.7%
palmitic acid 68–76%
stearic acid: 4–7.5%
linoleic acid: 8–10.5%
linolenic acid: 0.5–2%
oleic acid: 8–14%.

12. An improved composition for the treatment of hair or skin wherein the improvement comprises replacing animal origin fatty substances with a vegetable origin fatty substance composition comprising in % by weight of the total composition:
fatty acid triglycerides: 85 to 94%
fatty acid ester containing 40 carbon atoms: 7 to 14%
vitamins: 0.01 to 1.0%
antioxidant: 0.5 to 1.5%
    the average fatty acid composition of the triglycerides, expressed in % by weight, being as follows:
myristic acid: 0.35–0.7%
palmitic acid: 68–76%
stearic acid: 4–7.5%
linoleic acid: 8–10.5%
linolenic acid: 0.5–2%
oleic acid: 8–14%.

* * * * *